United States Patent
Ton et al.

(12)

(10) Patent No.: US 9,782,492 B2
(45) Date of Patent: Oct. 10, 2017

(54) STABILIZATION OF THERAPEUTIC AGENTS TO FACILITATE ADMINISTRATION

(71) Applicant: Allergan, Inc., Irvine, CA (US)

(72) Inventors: Jennifer L. Ton, Irvine, CA (US); Ronald C. Bates, Irvine, CA (US); Ji Zheng, Irvine, CA (US); Phillip P. Nguyen, Irvine, CA (US); Timothy E. O'Neill, Orange, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 15/048,393

(22) Filed: Feb. 19, 2016

(65) Prior Publication Data

US 2016/0166707 A1 Jun. 16, 2016

Related U.S. Application Data

(62) Division of application No. 13/516,986, filed as application No. PCT/US2010/060402 on Dec. 15, 2010, now abandoned.

(60) Provisional application No. 61/287,850, filed on Dec. 18, 2009.

(51) Int. Cl.
| | |
|---|---|
| *A61K 47/48* | (2006.01) |
| *G01N 27/447* | (2006.01) |
| *C07K 14/33* | (2006.01) |

(52) U.S. Cl.
CPC .. *A61K 47/48246* (2013.01); *A61K 47/48261* (2013.01); *C07K 14/33* (2013.01); *G01N 27/447* (2013.01)

(58) Field of Classification Search
None
See application file for complete search history.

(56) References Cited

U.S. PATENT DOCUMENTS

| | | |
|---|---|---|
| 7,354,740 B2 | 4/2008 | Xiang |
| 7,452,697 B2 | 11/2008 | Luo et al. |
| 2004/0028703 A1 | 2/2004 | Bigalke et al. |

FOREIGN PATENT DOCUMENTS

| | | |
|---|---|---|
| WO | 02-05844 A2 | 1/2002 |
| WO | 2006-010360 A2 | 2/2006 |

OTHER PUBLICATIONS

Edward J Schantz, Preparation and Characterization of Botulinum Toxin Type A for Human Treatment, Neurological Disease and Therapy, 1994, 41-49, 25, US.
John Chaddock, A Conjugate Composed of Nerve Growth Factor . . . , Growth Factors, Jan. 1, 2000, 147-155, 18 (2).
Marina Zdanovskaia, Recombinant Derivatives of Clostridial Neurotoxins as . . . , Jan. 1, 2000, 699-707, 19(8), Journal of Protein Chemistry.
Schantz, Edward J. et al, Properties and Use of Botulinum Toxin and Other Microbial Nerotoxins in Medicine, Microbiological Reviews, Mar. 1992, 80-99, 56 (1), US.

*Primary Examiner* — S. Devi
(74) *Attorney, Agent, or Firm* — Brigitte C. Phan; Ted A. Chan

(57) ABSTRACT

The present invention provides for a carrier complex for administration of therapeutic agents. In one aspect, an isolated *C. botulinum* carrier complex is provided, where the carrier complex lacks a native neurotoxin subunit.

13 Claims, No Drawings

STABILIZATION OF THERAPEUTIC AGENTS TO FACILITATE ADMINISTRATION

This is a Divisional of U.S. patent application Ser. No. 13/516,986, filed Dec. 14, 2012, now abandoned, which is a national stage application under 35 U.S.C. §371 of PCT patent application PCT/US2010/060402, filed on Dec. 15, 2010, which claims the benefit of U.S. Provisional Patent Application 61/287,850 filed Dec. 18, 2009, each of which is hereby incorporated by reference in its entirety.

BACKGROUND

The present disclosure relates to non-neurotoxin subunits of botulinum neurotoxin complexes, as utilized as a carrier for therapeutic agents. Botulinum toxins are proteins produced by the anaerobic bacterium *Clostridium botulinum*. There are seven immunologically distinct botulinum neurotoxins, which are designated botulinum neurotoxin serotypes A through G. Each complex consists of a neurotoxin subunit, a non-toxin non-hemagglutinin subunit and hemagglutinin subunits of various sizes and number, depending upon the serotype. The botulinum neurotoxin serotypes vary in the animal species they affect and the severity and duration of paralysis they evoke. The resulting neuroparalytic illness is referred to as botulism. See Preparation and Characterization of Botulinum Toxin Type A For Human Treatment, Schantz, E. J., et al, Therapy with Botulinum Toxin, 1994; v. 25: pp 41-49.

Botulism, or botulinum poisoning, can be caused by exposure to *C. botulinum*, which can grow in improperly sterilized and sealed foods or from botulinum spores, which are commonly found in soil. Symptoms of botulinum poisoning typically appear 18 to 36 hours after exposure to the bacterium or its spores. Botulinum toxin can pass unattenuated through the lining of the gut and can attack peripheral motor neurons. Symptoms of botulinum poisoning can include difficulty walking, swallowing, speaking, or in more extreme cases, death can result due to paralysis of respiratory muscles. Schantz, E. J. et al., Properties and use of Botulinum Toxin and Other Microbial Neurotoxins in Medicine, Microbiological Reviews, 1992 March, v. 1: pp 80-99.

While passing through the digestive tract, the hydrophobically-bound non-toxin subunits are thought to stabilize and protect the neurotoxin subunit. Protection is especially important for the toxin to pass through the low-pH portions of the digestive tract, which could otherwise denature the neurotoxin subunit. See Preparation and Characterization of Botulinum Toxin Type A For Human Treatment, Schantz, E. J., et al, Therapy with Botulinum Toxin, 1994; v. 25: pp 41-49.

Once the botulinum complex reaches the target neuron, the neurotoxin subunit disassociates from the remaining complex subunits and binds to the presynaptic membrane of the target neuron. The neurotoxin subunit binds to a cell surface receptor and is engulfed via receptor mediated endocytosis. The neurotoxin subunit, which is about 150 kDa, is comprised of a 100 kDa heavy chain portion and a 50 kDa light chain portion, the two portions linked by a disulfide bridge. The 100 kDa heavy chain enables the light chain to bind to the presynaptic membrane of the nerve cell and facilitates the transmembrane transfer of the light chain into the cytoplasm of the cell. The 50 kDa light chain is responsible for the inhibition of acetylcholine release. See Preparation and Characterization of Botulinum Toxin Type A For Human Treatment, Schantz, E. J., et al, Therapy with Botulinum Toxin, 1994; v. 25: pp 41-49.

Once the neurotoxin translocates through an endosomal membrane and enters the cytoplasm of the neuron, the light chain inhibits the release of acetylcholine, which interrupts signals normally transmitted from the nerve cell to neighboring muscle tissue. The result is local paralysis and relaxation of muscle tissue associated with the nerve cell.

Botulinum toxins have been used in the treatment of various neuromuscular disorders and conditions involving muscle spasm, as well as hyperhydrosis, cervical dystonia and blepharospasm.

Botulinum toxin is obtained by growing cultures of *C. botulinum* in a fermenter under anaerobic conditions, followed by harvesting and purifying the fermented mixture in accordance with known techniques to obtain the botulinum neurotoxin complex.

The protective and stabilizing effects provided by the non-toxin subunits can be useful to facilitate the enteric administration of other therapeutic agents that cannot withstand the extreme conditions of the human digestive tract, or to stabilize a therapeutic agent administered by other routes, such as intramuscular or subcutaneous injection, for example.

The present invention meets this need and provides for a carrier complex for administration of therapeutic agents. In one aspect, an isolated *C. botulinum* carrier complex, where the carrier complex lacks a native neurotoxin subunit, is provided.

DESCRIPTION

As used herein, the words or terms set forth below have the following definitions.

"About" means that the item, parameter or term so qualified encompasses a range plus or minus ten percent above and below the value of the stated item, parameter or term.

"Botulinum toxin" means a neurotoxin produced by *C. botulinum* and encompasses the botulinum toxin serotypes A, B, C, D, E, F and G.

A "carrier complex" means an association of at least two non-toxin protein subunits that form a complex, devoid of a native neurotoxin subunit.

A "native neurotoxin subunit" means the neurotoxin subunit naturally occurring (i.e. wild type) in a Botulinum toxin complex produced by *C. botulinum* bacteria.

As used here, the term "complex" refers to at least two non-toxin protein subunits, wherein the non-toxin protein subunits can be native or variant.

A "multi-subunit complex" means the association of proteins naturally produced by *C. botulinum* bacteria consisting of a neurotoxin subunit, a non-toxin non-hemagglutinin subunit and various hemagglutinin subunits.

An "open conformation" means the three-dimensional arrangement of the non-toxin subunit of a carrier complex which allows for the release of a native neurotoxin subunit, for example, or the addition and/or release of a therapeutic agent, while the non-toxin protein subunits maintain their association with each other.

A "closed conformation" means the three-dimensional arrangement of the non-toxin subunits of the carrier complex which does not allow for the removal of a neurotoxin subunit, or does not allow for the addition and/or release of a therapeutic agent, while the non-toxin protein subunits maintain their association with each other.

A "non-native therapeutic molecule" or a "non-native therapeutic agent" means a molecule or agent other than the native neurotoxin subunit that is naturally produced by *C. botulinum*.

A "modified multi-subunit complex" means a complex not naturally produced by *C. botulinum*, such as that produced by genetic engineering techniques.

A "non-native neurotoxin subunit" means a modified or recombinant neurotoxin molecule not naturally produced by *C. botulinum*.

"Naturally produced" means wild type.

A "therapeutic agent" or a "therapeutic molecule" is a molecule/agent that is biologically active or pharmaceutically active.

"Pharmaceutically active" means a chemically derived molecule or a small molecule that exhibits a desired and beneficial result or affect.

"Biologically active" means a non chemically derived molecule or a biologic that exhibits a desired and beneficial result or effect and that could be obtained from an organism. The organism can be, for example, a bacterium, yeast, etc.

A "modified organism" means one that is not naturally occurring, but which exists as the result of a directed change to the organism's genetic composition arising from the use of genetic engineering techniques.

A "non-native binding moiety" means a binding moiety of a botulinum neurotoxin that arises as a result of genetic engineering techniques.

A "modified *C. botulinum* bacterium" means a non-native form of *C. botulinum* bacterium, wherein at least one of its nucleic acids has been deleted, modified or replaced, as compared to a native or wild type *C. botulinum* bacterium.

A "non-native host" means a bacterium that does not naturally produce the proteins of the carrier complex.

A "recombinant multi-subunit complex" means a protein complex not naturally produced by *C. botulinum* and arising as a result of genetic engineering techniques. A recombinant multi-subunit complex can produced in a *C. botulinum* or a non *C. botulinum* bacterium.

"Variant" means that which is not native or naturally occurring.

A "ligand" means a binding element that can be attached to a carrier complex or a therapeutic molecule or agent for targeting/preferential binding purposes.

A "substrate" is a substance that can selectively bind to a ligand.

In one embodiment of the invention, the non-toxin subunits of the botulinum neurotoxin complex are utilized as a carrier complex for a therapeutic agent, wherein it is understood that the therapeutic agent does not include the native (i.e. a wild type) botulinum neurotoxin subunit naturally associated/produced with wild type non-toxin subunits (types and numbers).

In another embodiment of the invention, the multi-subunit complex produced by a *C. botulinum* bacterium is isolated and the 150 kDa neurotoxin subunit is removed, while the non-toxin subunits maintain association with each other. Once the neurotoxin subunit has been removed, a non-native therapeutic agent can be added to the carrier complex and retained by various molecular forces, as disclosed herein.

As utilized herein, a botulinum neurotoxin can be selected from the group consisting of botulinum toxin serotype A, B, C, D, E, F and G.

In another embodiment of the invention, a ligand can be joined and retained by the carrier complex by various molecular forces, as disclosed herein.

In another embodiment of the invention, a ligand and a therapeutic agent are joined together, and then joined to the carrier complex.

In another embodiment of the invention, a ligand and a therapeutic agent are individually joined to the carrier complex.

In yet another embodiment of the invention, a recombinant multi-subunit complex produced by a *C. botulinum* is isolated and the 150 kDa toxin subunit is removed, while the non-toxin subunits maintain association with each other. Once the neurotoxin subunit has been removed, a non-native therapeutic agent can be joined to/retained by the carrier complex by various molecular forces, as disclosed herein.

In another embodiment of the invention, the multi-subunit complex produced by a *Clostridium botulinum* is isolated and the subunits are completely disassociated from one another in solution. The neurotoxin subunit is then removed from solution and the remaining subunits properly reassociate relative to each other to form the carrier complex. Once the remaining non-toxin subunits reassociate, a non-native therapeutic agent can be joined to the complex by various molecular forces, as disclosed herein.

In another embodiment of the invention, the carrier complex is produced by a modified organism that does not produce a neurotoxin subunit. In yet another embodiment of the invention, the modified organism also produces a therapeutic agent in addition to the non-toxin subunits that make up the carrier complex. In a particular embodiment of the invention, the modified organism is a *C. botulinum* bacterium that does not produce a neurotoxin subunit or the organism can be another microbe, such as *E. coli* or yeast.

In one aspect, a method of obtaining the carrier complex is provided that includes isolating the multi-subunit complex in solution, followed by increasing the pH of the solution to about 9 to induce an open conformation, resulting in release of the neurotoxin subunit from the multi-subunit complex to thereby provide a carrier complex. In one embodiment, removal of the neurotoxin subunit from solution is achieved chromatographically by utilizing a cation exchange column, for example, and subsequently lowering the pH of the resulting eluent to about pH 6 to induce a closed conformation of the carrier complex.

In one embodiment of the invention, the method further comprises the addition of a therapeutic agent and/or a ligand to the carrier complex.

An embodiment of the invention comprises an isolated *C. botulinum* carrier complex, wherein the carrier complex lacks a native neurotoxin subunit and said carrier complex is capable of reversibly and controllably alternating between an open and a closed conformation. An embodiment can further comprise a non-native therapeutic molecule, or a ligand, or a therapeutic agent and a ligand. In some embodiments the carrier complex is a variant carrier complex, or a non-native therapeutic molecule, or a non-toxin non hemagglutinin subunit and a non-toxin hemagglutinin subunit. Some embodiments can further comprise a non-native neurotoxin subunit, or a non-toxin non hemagglutinin subunit and a non-toxin hemagglutinin subunit. In certain embodiments the non-native therapeutic molecule is a pharmaceutically active or biologically active molecule. In some embodiments the non-native therapeutic molecule is covalently associated with the complex, or is associated to the complex through hydrophobic interactions, or is associated to the carrier complex with ionic bonds, or is associated to the carrier complex with hydrogen bonds, or is associated to the carrier complex with Van der Waals interactions.

In certain embodiments the non-native therapeutic molecule is a pharmaceutically active or biologically active molecule, which can be covalently associated with the carrier complex, or associated with the complex through hydrophobic interactions, or associated with the carrier complex with ionic bonds, or associated to the carrier complex with hydrogen bonds, or is associated to the carrier complex with Van der Waals interactions.

Certain embodiments can comprise an isolated *C. botulinum* carrier complex of approximately 750 kDa, comprising a non-toxin non hemagglutinin subunit, an approximately 48 kDa non-toxin hemagglutinin subunit, an approximately 33 kDa non-toxin hemagglutinin subunit, an approximately 20 kDa non-toxin hemagglutinin subunit, an approximately 17 kDa non-toxin hemagglutinin subunit, and wherein the isolated carrier complex lacks a native neurotoxin subunit.

Certain embodiments can comprise an isolated *C. botulinum* carrier complex of approximately 500 kDa, comprising a non-toxin non hemagglutinin subunit, an approximately 70 kDa non-toxin hemagglutinin subunit, an approximately 33 kDa non-toxin hemagglutinin subunit, and an approximately 17 kDa non-toxin hemagglutinin subunit, wherein the isolated carrier complex lacks a native neurotoxin subunit.

Certain embodiments of the invention can comprise an isolated *C. botulinum* carrier complex of approximately 350 kDa, comprising a non-toxin non hemagglutinin subunit, an approximately 53 kDa non-toxin hemagglutinin subunit, an approximately 33 kDa non-toxin hemagglutinin subunit, an approximately 17 kDa non-toxin hemagglutinin subunit, and an approximately 22 kDa non-toxin hemagglutinin subunit, wherein the isolated carrier complex lacks a native neurotoxin subunit.

Certain embodiments of the invention can comprise an isolated *C. botulinum* carrier complex of approximately 350 kDa, comprising a non-toxin non hemagglutinin subunit, an approximately 70 kDa non-toxin hemagglutinin subunit, an approximately 33 kDa non-toxin hemagglutinin subunit, and an approximately 17 kDa non-toxin hemagglutinin subunit, wherein the isolated carrier complex lacks a native neurotoxin subunit.

Embodiments of the invention include a stabilized therapeutic molecule, comprising an isolated *C. botulinum* neurotoxin carrier complex, wherein a neurotoxin subunit has been removed, and a therapeutic molecule, wherein the therapeutic molecule is a non-native therapeutic molecule. In some embodiments the therapeutic molecule is a non-native therapeutic molecule, such as, for example, insulin.

Some embodiments include a modified organism producing a carrier complex, said carrier complex comprising a non-toxin non hemagglutinin subunit and a non-toxin hemagglutinin subunit, wherein said carrier complex lacks a neurotoxin subunit. In certain embodiments the carrier complex further comprises a non-native neurotoxin subunit having a non-native binding moiety.

Embodiments of the invention include a modified *C. botulinum* bacteria expressing a variant carrier complex, wherein the variant carrier complex lacks a neurotoxin subunit.

Some embodiments of the invention include a method of purifying a carrier complex derived from *C. botulinum*, the carrier complex lacking a native botulinum neurotoxin subunit, comprising isolating a native multi-subunit complex, disassociating the native multi-subunit complex into its constituent subunits, separating the native botulinum neurotoxin subunit therefrom, and re-associating remaining subunits into the carrier complex, thereby producing a carrier complex lacking a native botulinum neurotoxin subunit. Certain embodiments include the carrier complex thereby purified. Certain embodiments include the step of associating a non-native therapeutic molecule to the carrier complex covalently.

Embodiments of the invention include a method of purifying an about 750 kDa carrier complex from an about 900 kDa carrier complex comprising isolating the 900 kDa carrier complex, disassociating the 900 kDa carrier complex into its constituent subunits, separating an about 150 kDa neurotoxin subunit therefrom and re-associating remaining subunits into the 750 kDa carrier complex, thereby producing a 750 kDa carrier complex lacking a native botulinum neurotoxin subunit.

Embodiments of the invention include a method of purifying an about 500 kDa carrier complex from an about 650 kDa carrier complex comprising isolating the 650 kDa carrier complex, disassociating the 650 kDa carrier complex into its constituent subunits, separating an about 150 kDa neurotoxin subunit therefrom and re-associating remaining subunits into the 500 kDa carrier complex, thereby producing a 500 kDa carrier complex lacking a native botulinum neurotoxin subunit.

Embodiments of the invention include a method of purifying an about 350 kDa carrier complex from an about 500 kDa carrier complex comprising isolating the 500 kDa carrier complex, disassociating the 500 kDa carrier complex into its constituent subunits, separating an about 150 kDa neurotoxin subunit therefrom and re-associating remaining subunits into the 350 kDa carrier complex, thereby producing a 350 kDa carrier complex lacking a native botulinum neurotoxin subunit.

Embodiments of the invention include a method of purifying an about 150 kDa carrier complex from an about 300 kDa carrier complex comprising isolating the 300 kDa carrier complex, disassociating the 300 kDa carrier complex into its constituent subunits, separating an about 150 kDa neurotoxin subunit therefrom and re-associating remaining subunits into the 150 kDa carrier complex, thereby producing a 150 kDa carrier complex lacking a native botulinum neurotoxin subunit.

Embodiments of the invention include a method of purifying an about 130 kDa carrier complex from an about 280 kDa carrier complex comprising isolating the 280 kDa carrier complex, disassociating the 280 kDa carrier complex into its constituent subunits, separating an about 150 kDa neurotoxin subunit therefrom and re-associating remaining subunits into the 130 kDa carrier complex, thereby producing a 130 kDa carrier complex lacking a native botulinum neurotoxin subunit. Additional embodiments can include associating a non-native therapeutic molecule to the 750 kDa carrier complex covalently, or associating a non-native therapeutic molecule to the 500 kDa carrier complex covalently, or associating a non-native therapeutic molecule to the 350 kDa carrier complex covalently, or associating a non-native therapeutic molecule to the 150 kDa carrier complex covalently, or associating a non-native therapeutic molecule to the 130 kDa carrier complex covalently.

In certain embodiments of the invention, the native multi-subunit complex is derived from *C. botulinum* Type A, *C. botulinum* Type B, *C. botulinum* Type C, *C. botulinum* Type D, *C. botulinum* Type E, *C. botulinum* Type F or *C. botulinum* Type G.

Embodiments of the invention include a method of purifying a variant carrier complex lacking a neurotoxin subunit, wherein the variant carrier complex is expressed from a non-native host, comprising isolating a variant carrier complex, disassociating the variant complex into its constituent subunits, separating a botulinum neurotoxin subunit therefrom, and re-associating remaining variant complex subunits into the variant carrier complex, thereby producing the variant carrier complex lacking a neurotoxin subunit expressed from a non-native host, wherein the variant carrier complex is capable of reversibly and controllably alternating between an open and a closed conformation. Certain embodiments can include covalently associating the carrier complex lacking a botulinum neurotoxin subunit to a non-native therapeutic molecule, or associating the carrier complex lacking a botulinum neurotoxin subunit to a non-native therapeutic molecule through hydrophobic interactions, or ionically associating the complex to a non-native therapeutic molecule.

Embodiments of the invention include a method for stabilizing a therapeutic molecule comprising isolating a *C. botulinum* carrier complex, wherein a neurotoxin subunit has been removed and associating said carrier complex with said therapeutic molecule to thereby stabilize said therapeutic molecule.

Embodiments of the invention can include a method of purifying a *C. botulinum* carrier complex devoid of a botulinum neurotoxin subunit, wherein non neurotoxin subunits maintain inter-subunit association, comprising isolating a carrier complex containing a botulinum neurotoxin subunit and removing the botulinum neurotoxin subunit, thereby producing the *C. botulinum* carrier complex devoid of the botulinum neurotoxin subunit. In certain embodiments the removing step includes raising the pH of a carrier complex containing solution to induce an open conformation of the carrier complex, thereby disassociating the botulinum neurotoxin subunit from the carrier complex, binding the botulinum neurotoxin subunit to a substrate to remove the botulinum neurotoxin subunit from the carrier complex containing solution and lowering the pH of the carrier complex containing solution to induce a closed conformation of the carrier complex, thereby removing the botulinum neurotoxin subunit. In certain embodiments the *C. botulinum* carrier complex is derived from *C. botulinum* Type A, *C. botulinum* Type B, *C. botulinum* Type C, *C. botulinum* Type D, *C. botulinum* Type E, *C. botulinum* Type F or *C. botulinum* Type G. In some embodiments the substrate is cationic, or anionic, or a hydrophobic substrate, or a mixed mode substrate. In some embodiments the subunit components are variant subunit components and expressed from a non-native host.

Embodiments of the invention include a method of purifying an about 750 kDa carrier complex comprising isolating an about 900 kDa carrier complex and removing an about 150 kDa neurotoxin subunit therefrom, producing the purified the 750 kDa carrier complex, wherein integrity of the 750 kDa complex is maintained throughout purification and the carrier complex is capable of reversible conformational change between an open and closed conformation.

Embodiments of the invention include a method of purifying an about 500 kDa carrier complex comprising isolating an about 650 kDa carrier complex and removing an about 150 kDa neurotoxin subunit therefrom, producing the 500 kDa carrier complex, wherein the integrity of the 500 kDa complex is maintained throughout purification and the carrier complex is capable of reversible conformational change between an open and closed conformation.

Embodiments of the invention include a method of purifying an about 350 kDa carrier complex comprising isolating an about 500 kDa carrier complex and removing an about 150 kDa neurotoxin subunit therefrom, producing the 350 kDa carrier complex, wherein the integrity of the 350 kDa complex is maintained throughout purification and the carrier complex is capable of reversible conformational change between an open and closed conformation.

Embodiments of the invention include a method of purifying an about 150 kDa carrier complex comprising isolating an about 300 kDa carrier complex and removing an about 150 kDa neurotoxin subunit therefrom, producing the 150 kDa carrier complex, wherein the integrity of the 150 kDa complex is maintained throughout purification and the carrier complex is capable of reversible conformational change between an open and closed conformation.

Embodiments of the invention include a method of purifying an about 130 kDa carrier complex comprising isolating an about 280 kDa carrier complex and removing an about 150 kDa neurotoxin subunit therefrom, producing the 130 kDa carrier complex, wherein the integrity of the 130 kDa complex is maintained throughout purification and the carrier complex is capable of reversible conformational change between an open and closed conformation.

Embodiments of the invention include a method for stabilizing a non-native therapeutic molecule for enteric administration comprising isolating a carrier complex containing a botulinum neurotoxin subunit, removing the botulinum neurotoxin subunit from the carrier complex and associating the non-native therapeutic molecule to the carrier complex, thereby stabilizing the non-native therapeutic molecule for enteric administration.

The non-toxin subunits of the multi-subunit complex produced by *C. botulinum* are thought to protect and stabilize the neurotoxin subunit of the complex from unfavorable conditions found in the human digestive tract, including extremely low pH and the presence of proteases and other enzymes that can denature the neurotoxin subunit. If properly protected, the neurotoxin subunit will able to function at the target site. When the neurotoxin subunit is removed from the multi-subunit complex, under proper conditions, the non-toxin subunits can function as and provide a carrier complex for a non-native therapeutic molecule, or a ligand, or both a therapeutic agent and a ligand together, to pass through the digestive tract, or provide stabilization or protective function for the non-native therapeutic molecule, for example, when the carrier complex associated with the non-native therapeutic molecule is injected locally to a target site. This allows the non-native therapeutic agent to function at its target site where it will exert its effect, while the carrier complex provided in accordance with the teachings of the present disclosure provide increased protection/stability to the non-native therapeutic agent than if administered alone (i.e. non-native therapeutic agent without association to the carrier complex).

The carrier complex is capable of reversibly and controllably alternating between an open and closed conformation. The open conformation allows for the non-toxin subunits to maintain association with one another while allowing the neurotoxin subunit to be removed and replaced with a non-native therapeutic agent and/or a ligand. Upon replacement with a non-native therapeutic agent and/or a ligand, the carrier complex can, under appropriate conditions detailed below, revert back to a closed conformation, where the carrier complex now protects the non-native therapeutic molecule and/or the ligand from unfavorable environmental conditions.

In particular embodiments, a ligand can be attached to the carrier complex or to the non-native therapeutic molecule.

Where the ligand is attached to the therapeutic agent, the therapeutic agent is then associated to the carrier complex.

In one embodiment of the invention, alternating conformations of the carrier complex between an open and closed conformation is induced by changing the pH of the solution in which the carrier complex is contained. Where the pH of the carrier complex containing solution is increased to between about 8 and about 10, an open conformation is induced, and where the pH of the carrier complex containing solution is decreased to about 2 and about 7, a closed conformation is induced.

The carrier complex can consist of non-toxin proteins natively produced by C. botulinum, or the carrier complex can be produced using genetic engineering techniques. In a preferred embodiment of the invention, the non-toxin proteins of the carrier complex are produced by C. botulinum type A, that is, the carrier complex is derived from the multi-subunit complex naturally produced by C. botulinum bacteria, wherefrom the natively associated botulinum neurotoxin subunit is removed and thus provide a carrier complex. In one example, C. botulinum type A non-toxin proteins include an about 130 kDa non-toxin non hemagglutinin subunit, an about 52 kDa hemagglutinin subunit, an about 35 kDa hemagglutinin subunit, an about 20 kDa hemagglutinin subunit, and an about 15 kDa hemagglutinin subunit. In one example, a carrier complex can comprise all of the non-toxin subunits of the multi-subunit complex derived from a type A multi-subunit complex or the invention can consist of a selection of the non-toxin subunits of the multi-subunit complex, that is two or more of the non-toxin subunits derived from a type A multi-subunit complex.

In another embodiment, the non-toxin subunits of the carrier complex are produced by C. botulinum type B, that is the carrier complex is derived from the multi-subunit complex naturally produced by C. botulinum type B. C. botulinum type B non-toxin proteins include an about 130 kDa non-toxin non hemagglutinin subunit, an about 70 kDa hemagglutinin subunit, an about 33 kDa hemagglutinin subunit, and an about 17 kDa hemagglutinin subunit. In a particular embodiment, a carrier complex can include all of the non-toxin subunits derived from a type B multi-subunit complex or can consist of a selection of the non-toxin subunits, that is, two or more of the non-toxin subunits derived from a type B multi-subunit complex.

In another embodiment, the non-toxin subunits of the carrier complex are produced by C. botulinum type C, that is the carrier complex is derived from the multi-subunit complex naturally produced by C. botulinum type C. C. botulinum type C non-toxin proteins include an about 130 kDa non-toxin non hemagglutinin subunit, an about 53 kDa hemagglutinin subunit, an about 33 kDa hemagglutinin subunit, an about 22 kDa hemagglutinin subunit, and an about 17 kDa hemagglutinin subunit. In a particular embodiment, a carrier complex can include all of the non-toxin subunits derived from a type C multi-subunit complex or can consist of a selection of the non-toxin subunit of the multi-subunit complex, that is, two or more of the non-toxin subunits derived from a type C multi-subunit complex.

The non-toxin subunits of the carrier complex can be produced by any of the Clostridium botulinum serotypes, thus the carrier complex can comprise all of the non-toxin subunits of a multi-subunit complex produced by any of the C. botulinum serotypes or the invention can consist of a selection of two or more of the non-toxin subunits of a multi-subunit complex produced by C. botulinum. The non-toxin subunits can all be from one particular C. botulinum type to give rise to a carrier complex, or can be a combination of non-toxin proteins of various C. botulinum types. For example, and not limited to, hemagglutinin subunits from a C. botulinum type A may be combined with non-toxin non hemagglutinin subunit from a C. botulinum type C.

For example, it is further contemplated that a carrier complex can comprise non-toxin subunits from various C. botulinum serotypes. For example, and not limited to, 130 kDa non-toxin non-hemagglutinin subunits from C. botulinum type A, 70 kDa hemagglutinin from C. botulinum type B, 33 kDa hemagglutinin from C. botulinum type C, 22 kDa hemagglutinin from C. botulinum type C, 15 kDa hemagglutinin from C. botulinum type A in any useful number or combination In another embodiment, the non-toxin subunits that make up the carrier complex are produced by E. coli. As an example, the carrier complex can be comprised of non-toxin subunits from different native strains that are combined to make up a variant carrier complex that is produced and isolated from E. coli.

It is to be understood that a carrier complex may be provided by either a Clostridium or genetically transformed non Clostridium bacteria or genetically transformed mammalian cell line such as, for example CHO or NSO. In another embodiment of the invention, the carrier complex can be produced by a bacterium, such as E. coli, that does not produce a neurotoxin subunit. Accordingly, in such bacteria, only the non-toxin subunits are produced by the bacterium, thus giving rise to a carrier complex straight away, without requiring the removal of a neurotoxin subunit. Using existing recombinant DNA technology, the bacterium, such as E. coli, can be engineered to produce the individual subunits which could then be folded into the desired configuration using existing refolding techniques.

In one embodiment of the invention, the carrier complex is produced by growing C. botulinum bacteria in a fermenter, under anaerobic conditions, using media comprised of soy peptone, yeast and glucose. Once grown, the multi-subunit complex can be purified from fermentation broth using known purification techniques, such as chromatography or acid precipitation, per the Schantz method. See Preparation and Characterization of Botulinum Toxin Type A For Human Treatment, Schantz, E. J., et al, Therapy with Botulinum Toxin, 1994; v. 25: pp 41-49. Chromatographic method and system for purifying a botulinum toxin, Luo, et al. (U.S. Pat. No. 7,452,697), Animal product free system and process for purifying a botulinum toxin, Xiang et at. (U.S. Pat. No. 7,354,740), all of which are herein incorporated by reference in their entirety. Once the multi-subunit complex, which includes the neurotoxin subunit, is purified from host cell proteins the neurotoxin subunit is isolated from the non-toxin subunits and removed in accordance with the teachings provided herein, to provide a carrier complex.

In one aspect, there is provided a method for purifying the multi-subunit complex from a fermentation broth, thus providing a solution containing a purified form of the multi-subunit complex from which the carrier complex is isolated. The pH of the multi-subunit complex containing solution is subsequently increased to a pH of between about 8 and about 10, preferably from about pH 8.5 to about 9.5, more preferably to a pH of about 9. The increase in pH results in disassociation of the neurotoxin subunit from the remaining non-toxin subunits of the multi-subunit complex. In one example, the neurotoxin subunit (now in solution and dissociated from the multi-subunit complex) is then bound to a cationic substrate, resulting in a solution containing the carrier complex that is devoid of the neurotoxin subunit. The anionic substrate can be, for example, SP SEPHAROSE® HP manufactured by GE Healthcare Life Sciences, 50HS manufactured by Poros or TOYOPEARL® S-650M manufactured by Tosoh Biosciences.

The pH of the carrier complex containing solution, the eluate, can then be lowered to a pH of between about 5 and about 7, preferably to a pH of about 6 to induce a closed conformation. The pH is lowered to stabilize the carrier complex, for allowing the carrier complex to remain at a pH above 7 can result in instability of carrier complex subunits. The pH of the carrier complex containing solution can later be raised to induce an open configuration to allow for the addition of a therapeutic agent and/or a ligand. In another embodiment, a therapeutic agent and/or a ligand is added to the solution prior to the induction of a closed conformation, that is, while the carrier complex is in an open configuration and the neurotoxin subunit has been removed from the solution. Once the therapeutic agent and/or the ligand is added to the carrier complex, a closed configuration can be induced by lowering the pH of the carrier complex containing solution.

It is also contemplated that the neurotoxin subunit can be bound to a cationic substrate. The cationic substrate can be, for example, Q SEPHAROSE® HP manufactured by GE, 50HQ manufactured by Poros or Macroprep High Q manufactured by Biorad. The neurotoxin subunit can bind to a cationic substrate at a conductivity of between about 5 mS/cm and 10 mS/cm at a pH of between about pH 7 and about pH 9, preferably at a pH of about 8. The carrier complex will not bind to an anionic substrate in this conductivity range, thus the carrier complex will be in a solution void of a neurotoxin subunit.

In yet another embodiment, the neurotoxin subunit is bound to a hydrophobic substrate. The hydrophobic substrate can be, for example, Butyl S SEPHAROSE® HP manufactured by GE, TOYOPEARL® Butyl 650M manufactured by Tosoh Biosciences or TOYOPEARL® Phenyl 650M manufactured by Tosoh Biosciences. The neurotoxin subunit and the carrier complex can be bound to Butyl S SEPHAROSE® HP in 1M ammonium sulfate. The neurotoxin subunit can be eluted at 0.5-0.3M ammonium sulfate. The carrier complex can be eluted at 0.2M ammonium sulfate.

In yet another embodiment, the neurotoxin subunit is bound to a mixed mode substrate. The mixed mode substrate can be, for example, MEP Hypercel manufactured by Pall or Capto MMC manufactured by GE. The neurotoxin subunit and the carrier complex can bind to the substrate in low salt and can be eluted separately using an increasing linear salt gradient up to 1M sodium chloride, for example.

The temperature for disassociation of the neurotoxin subunit from the remaining non-toxin subunits of the multi-subunit complex can be from about 1° C. to about 60° C., in another embodiment of the invention, the temperature for dissociation is between about 4° C. to about 40° C. In yet another preferred embodiment, the temperature for disassociation of the neurotoxin subunit from the remaining non-toxin subunits of the multi-subunit complex can from about 32° C. to about 40° C.

The incubation time for disassociation of the neurotoxin subunit from the remaining non-toxin subunits of the multi-subunit complex can be from about 1 minute to about 48 hours, in a preferred embodiment, the incubation time is from about 2 hours to about 24 hours. In yet another preferred embodiment, the incubation time is from about 10 hours to about 20 hours.

In another embodiment of the invention, the carrier complex is bound to a cationic substrate for separation from the neurotoxin subunit. The carrier complex can bind to a cationic substrate at a conductivity of between about 10 mS/cm and 20 mS/cm at a pH of between about pH 7 and about pH 9, preferably to a pH of about 8. The neurotoxin subunit will not bind to a cationic substrate in this conductivity range, thus the carrier complex can be eluted off of the substrate and can be in a solution devoid of a neurotoxin subunit.

The carrier complex can also be bound to a cationic substrate, a hydrophobic substrate or a mixed mode substrate. The cationic substrate can be, for example, Q SEPHAROSE® HP manufactured by GE, 50HQ manufactured by Poros or Macroprep High Q manufactured by Biorad. The anionic substrate can be, for example, SP SEPHAROSE® HP manufactured by GE, 50HS manufactured by Poros or TOYOPEARL® S-650M manufactured by Tosoh Biosciences. The hydrophobic substrate can be, for example, Butyl SEPHAROSE® manufactured by GE, TOYOPEARL® Butyl 650M manufactured by Tosoh Biosciences or TOYOPEARL® Phenyl 650M manufactured by Tosoh Biosciences. The mixed mode substrate can be, for example, MEP Hypercel manufactured by Pall or CAPTO® MMC manufactured by GE.

The carrier complex can also be produced by purifying the multi-subunit complex from host cell proteins, followed by disassociation of the subunits of the multi-subunit complex from one another. The subunits of the multi-subunit complex, including the neurotoxin subunit, can be completely disassociated from each other using organic solvents, such as acetonitrile, for example. The concentration of acetonitrile in solution can be from 1% to 100%, in a preferred embodiment the concentration of acetonitrile in solution is between about 15% and about 20%. The organic solvent can be mixed with an aqueous buffer or water. An example of an aqueous buffer than can be used is sodium phosphate. In one embodiment of the invention, the concentration of sodium phosphate in solution can be between 10 mM and 150 mM. The temperature for disassociation to occur can be between about 1° C. to about 60° C., and in a preferred embodiment, the temperature for dissociation is between about 4° C. to about 37° C.

The neurotoxin subunit, now released and no longer associated with non-toxin subunits, is then bound to a hydrophobic substrate. The hydrophobic substrate can be Silica C-2, Silica C-4, Silica C-8, Silica C-10, Silica C-18, Polymeric C-4, or Polymeric C-8, for example. In one example, the neurotoxin subunit can bind to a hydrophobic substrate in the presence of organic solvents equal to the percentage of organic solvents present for dissociation.

Upon removal of the neurotoxin subunit, such as by binding to a hydrophobic substrate, some or all of the non-toxin subunits can reassociate to form the carrier complex. Reassociation can occur by dialyzing the organic solvent out of the solution, diluting the organic solvent with an aqueous solution, evaporating the organic solvent or centrifuging and extracting the organic phase from the aqueous phase. In one example, following reassociation, an open conformation of the carrier complex is induced by increasing the pH of the carrier complex containing solution to between about 8 and about 10 pH units, preferably to a pH of about 9, and a non-native therapeutic molecule is joined/associated to the complex. A closed configuration can be subsequently induced by lowering the of the carrier complex containing solution to between about 2 and about 7 pH units, preferably to a pH of about 6.5, for example.

In another embodiment, the non-toxin subunits are separated from each other using a solution high in conductivity, such as and for example, but not limited to, a solution with a high concentration of sodium chloride. The concentration of sodium chloride can be about 0.5M to about 2M. The incubation time of the carrier complex in said solution can be from about 1 minute to about 24 hours, in a preferred embodiment, the incubation time is from about 3 hours to about 24 hours. In yet another preferred embodiment, the incubation time is from about 7 hours to about 10 hours.

In another embodiment, the non-toxin subunits are separated from each other using a high pH solution. The pH of the solution can be from a pH of about 7 to a pH of about 10. The incubation time of the multi-subunit complex in said solution can be from about 1 minute to about 24 hours. In a preferred embodiment, the incubation time in said solution is from about 3 hours to about 24 hours.

The carrier complex can precipitate out of solution when the pH of the solution is in the range of about 6.5 to a pH of about 7. However, maintaining a favorable conductivity of the carrier complex containing solution has a stabilizing effect in this particular pH range. For example, the carrier complex is stable in the pH range of about 6.5 to about 7 when about 0.3M sodium chloride is added to the carrier complex containing solution.

In another embodiment, the non-toxin subunits are separated from the neurotoxin subunit utilizing gel electrophoresis. The multi-subunit complex subunits disassociate from one another with the addition of sodium dodecyl sulfate, an anionic detergent that denatures secondary and non-disulfide-linked tertiary structures. An electrical current runs through the gel allowing the subunits to migrate across the gel based on their molecular weight. Protein bands can be excised from the gel and solubilized with acetonitrile. The solution is then centrifuged and the supernatant is subsequently treated and stored in formic acid.

In another embodiment, the non-toxin subunits are separated from the neurotoxin subunit utilizing capillary electrophoresis.

Particular non-toxin subunits, so isolated from the gel run, are selected for reassociation to provide the carrier complex in accordance with the teachings of the present disclosure. In another embodiment, a non-native therapeutic agent and/or a ligand is added to the non neurotoxin subunit containing solution before the non-toxin subunits reassociate. In one example, the therapeutic agent and/or the ligand is joined to the complex simultaneously as the non-toxin subunits reassociate.

Therapeutic agents can be, for example but not limited to, proteins, antibodies, DNA, RNA, steroids, enzymes, growth factors or hormones, such as insulin. Ligands can be, for example, but not limited to virus particles, fluorescent dyes, radioactive compounds or chemical lamination compounds. Thus in particular embodiments, the carrier complex can comprise both a therapeutic agent and a ligand simultaneously. The carrier complex can also comprise only a therapeutic agent or a ligand; or can also comprise a therapeutic agent to which a ligand is attached.

In another embodiment, targeting of the non-native therapeutic agent or the carrier complex carrying the therapeutic agent can be followed by the addition of a detectable ligand to the non-native therapeutic agent and/or to the non-toxin subunits of the carrier complex by, for example, but not limited to, hydrogen bonding, covalent linkage or ionic interaction.

We claim:

1. A method of producing a carrier complex derived from a native multi-subunit botulinum toxin complex comprising a native neurotoxin subunit and native non-toxin subunits, the carrier complex devoid of the botulinum neurotoxin subunit, the method comprising the steps of:
   (a) isolating the native multi-subunit botulinum toxin complex from *Clostridium botulinum* bacteria using an animal product free system and process;
   (b) disassociating the native multi-subunit botulinum toxin complex from step (a) into its constituent neurotoxin and non-toxin subunits in a solution;
   (c) separating the disassociated native neurotoxin subunit from the disassociated native non-toxin subunits;
   (d) separating the disassociated native non-toxin subunits one from another;
   (e) selecting at least two of the separated-non-toxin subunits from step (d);
   (f) isolating the at least two separated non-toxin subunits; and
   (g) re-associating the at least two isolated non-toxin subunits, thereby producing the carrier complex.

2. The method of claim 1 further comprising the step of adding a non-native therapeutic agent to the re-associated at least two non-toxin subunits.

3. The method of claim 1 further comprising the step of adding a ligand to the re-associated at least two non-toxin subunits.

4. The method of claim 1, wherein the separating the non-toxin subunits is carried out in a solution high in conductivity, the high conductivity being equivalent to that of a solution comprising about 0.5 M to about 2.0M sodium chloride.

5. The method of claim 1, wherein the separating the non-toxin subunits is carried out in a solution having a pH of about 7 to about 10.

6. The method of claim 4, wherein the separating the non-toxin subunits is carried out in a solution, having a pH range of about 7 to about 10.

7. The method of claim 1, wherein the separating the neurotoxin subunit from the non-toxin subunits is achieved chromatographically.

8. The method of claim 2, wherein the non-native therapeutic agent is a protein, a nucleic acid, a growth factor, or a combination thereof.

9. The method of claim 3, wherein the ligand is selected from the group consisting of virus particles, fluorescent dyes, and radioactive compounds.

10. The method of claim 2, further comprising the step of adding a ligand to the re-associated at least two non-toxin subunits.

11. The method of claim 10, wherein the therapeutic agent and the ligand are joined simultaneously to the re-associated at least two non-toxin subunits.

12. The method of claim 1, further comprising the step of adding a non-toxin subunit isolated from a second native multi-subunit complex from a different serotype of botulinum toxin to the isolated at least two non-toxin subunits prior to the step of re-association.

13. The method of claim 12, wherein the second native multi-subunit complex from the different serotype of the botulinum toxin is selected from the group consisting of botulinum toxin type A, botulinum toxin type B, botulinum toxin type C, botulinum toxin type D, botulinum toxin type F and botulinum toxin type G.

* * * * *